(12) United States Patent
Johnson et al.

(10) Patent No.: US 8,140,352 B2
(45) Date of Patent: Mar. 20, 2012

(54) ORDER SETS HAVING DIFFERENT VIEWS FOR CPOE SYSTEMS

(75) Inventors: Christopher David Johnson, San Francisco, CA (US); Roni Fischman Zeiger, Mountain View, CA (US)

(73) Assignee: Performance Clinical Systems, LLC, San Francisco, CA (US)

( * ) Notice: Subject to any disclaimer, the term of this patent is extended or adjusted under 35 U.S.C. 154(b) by 315 days.

(21) Appl. No.: 11/969,133

(22) Filed: Jan. 3, 2008

(65) Prior Publication Data

US 2008/0189135 A1     Aug. 7, 2008

Related U.S. Application Data

(60) Provisional application No. 60/878,379, filed on Jan. 3, 2007.

(51) Int. Cl.
*G06Q 50/00*     (2006.01)
(52) U.S. Cl. .................... 705/2; 705/3; 600/300
(58) Field of Classification Search .......... 705/2, 3, 705/4; 707/100; 702/19
See application file for complete search history.

(56) References Cited

U.S. PATENT DOCUMENTS

| | | | |
|---|---|---|---|
| 7,069,227 B1 * | 6/2006 | Lintel et al. | 705/4 |
| 7,181,375 B2 * | 2/2007 | Rao et al. | 703/2 |
| 7,260,480 B1 * | 8/2007 | Brown et al. | 702/19 |
| 2003/0125989 A1 * | 7/2003 | Abraham-Fuchs | 705/3 |
| 2006/0036619 A1 * | 2/2006 | Fuerst et al. | 707/100 |
| 2006/0074720 A1 * | 4/2006 | Brutting et al. | 705/3 |
| 2007/0027717 A1 * | 2/2007 | Karamchedu et al. | 705/3 |
| 2007/0168461 A1 | 7/2007 | Moore | |
| 2007/0185739 A1 * | 8/2007 | Ober et al. | 705/3 |
| 2007/0260492 A1 * | 11/2007 | Feied et al. | 705/3 |
| 2008/0077436 A1 * | 3/2008 | Muradia | 705/2 |
| 2008/0221927 A1 * | 9/2008 | Levy | 705/3 |
| 2008/0235049 A1 | 9/2008 | Morita et al. | |
| 2008/0256181 A1 | 10/2008 | Morita et al. | |
| 2009/0089093 A1 | 4/2009 | Johnson et al. | |

OTHER PUBLICATIONS

"Structuring Order Sets for Interoperable Distribution" by James McClay, MS, MD, James R Campbell, MD, Craig Parker, MD, Karen Hrabak, MSN, RNC, Samson W. Tu MS, and Robert Abarnanel, MD, PhD dated 2006, pp. 549-553.*
Google search history, Mar. 9, 2010.*
"Use of Medical Subject Headings in Metadata", Letters to Doctor James Carmichael and son, Rector and Visitors of the University of Virginia, 2005.*

(Continued)

*Primary Examiner* — Dilek B Cobanoglu
(74) *Attorney, Agent, or Firm* — Beyer Law Group LLP

(57) ABSTRACT

Order sets are presented in different views thereby allowing the doctor to treat a patient in a more intuitive manner. Order set content is created so that order sets can be viewed from varying perspectives. An order set library is modified such that each order statement or orderable is tagged with metadata. Each orderable is tagged with an Intervention tag, a Problem tag, and a System tag. An application may then take the modified order sets and present them to doctors based on an Intervention view, a Problem view, or a System view. These views give the doctor the option of switching between views depending on the severity of a patient's medical condition and allows the doctor to follow a more intuitive and internal mental process when treating a patient. The doctor does not have to translate between different perspectives of the order sets mentally, thereby greatly reducing the doctor's cognitive load.

4 Claims, 8 Drawing Sheets

OTHER PUBLICATIONS

International Search Report dated May 4, 2010 in PCT App. No. PCT/US10/28537.

Written Opinion dated May 4, 2010 in PCT App. No. PCT/US10/28537.

Schnipper et al. "Smart Forms in an Electronic Medical Record: Documentation-based Clinical Decision Support to Improve Disease Management"; Journal of the American Medical Information Assoc.; vol. 15, No. 4, Published Aug. 2008, (retrieved Apr. 22, 2010). from the internet URL http://www.ncbl.rlm.nlh.gov/pmc/articles/PMC2442258/pdf/513.S1067502708000625.main.pdf, entire document.

* cited by examiner

FIG. 3A

Stone
Stepping Checkout system    302    ⌂ home 🔒 sign off ? guide
                                           QUICKORDERS
                                           The Problem-Based Order Writing System > Patient > Problems > Orders > Review

Step 2: Problems

Test Patient / MR=5315315

Admit to

Unit
○ (Any)          ☑ Add the unit's order set to the orders
○ Med/Surg         (Quick Admission)
○ Critical Care    (Med/Surg Admission)
○ Telemetry        (Intensive Care Unit/Critical Care Admission)
● None             (Telemetry Admission)

Primary problems

Type a problem name or select: [          ]

Total # Order Set: 16

| Select Problem | 306 | Specialty | Phase of care | Time used | Favorite |
|---|---|---|---|---|---|
| ☐ Diabetes Mellitus (DM) | | Endocrinology | Comorbid | 22 | |
| ☐ Cellulitis | | Infectious Disease | Admission | 18 | |
| ☐ Unstable Angina/NSTEMI | | Cardiology | Admission | 17 | ☆ |
| ☐ Acute Pancreatitis | | Gastroenterology | Admission | 9 | |
| ☐ General Elderly / 'Weak and Dizzy' | | Internal Medicine | Admission | 7 | |
| ☐ Chest Pain | | Cardiology | Admission | 5 | ☆ |
| ☐ Chronic Kidney Disease (CKD)(CRI) | | Nephrology | Comorbid | 5 | |

Stone
Stepping Checkout system
⌂home 🔒sign off ? guide
QUICKORDERS
The Problem-Based Order Writing System 〉Patient 〉Problems 〉Orders 〉Review〉

Step 2: Problems

Test Patient / MR=5315315

Admit to

Unit
○ (Any)          ☑ Add the unit's order set to the orders
○ Med/Surg         (Quick Admission)
○ Critical Care    (Med/Surg Admission)
○ Telemetry        (Intensive Care Unit/Critical Care Admission)
⦿ None             (Telemetry Admission)

_304_

Primary problems

Type a problem name or select: [      ]                                    Total # Order Set: 16

| Select Problem | Specialty | Phase of care | Time used | Favorite |
|---|---|---|---|---|
| ☑ Diabetes Mellitus (DM) | Endocrinology | Comorbid | 22 | 🔍 |
| ☐ Cellulitis | Infectious Disease | Admission | 18 | 🔍 |
| ☑ Unstable Angina/NSTEMI | Cardiology | Admission | 17 | ☆ 🔍 |
| ☐ Acute Pancreatitis | Gastroenterology | Admission | 9 | 🔍 |
| ☐ General Elderly / 'Weak and Dizzy' | Internal Medicine | Admission | 7 | 🔍 |
| ☐ Chest Pain | _306_ Cardiology | Admission | 5 | ☆ 🔍 |
| ☑ Chronic Kidney Disease (CKD)(CRF) | Nephrology | Comorbid | 3 | 🔍 |

Stone
Stepping Checkout system

🏠 home 🔒 sign off ? guide
QUICKORDERS
The Problem-Based Order Writing System

> Patient > Problems > Orders > Review

Step 3: Orders

▼ Problem
  ▼ Unstable Angina/NSTEMI
  ▼ Diabetes Mellitus (DM)
  ▼ Chronic Kidney Disease (C
  ▼ Med/Surg Admission
  › Intervention
  › System
    316

Allergies

Medications ordered
UAng Please see medicatio

Test Patient / MR=5315315

| Problem | |
|---|---|
| Unstable Angina/NSTEMI | |
| Medications | |

☑ 🔍 Please see medication reconciliation list for additional medications
☐ aspirin 325 [4x81] milligram tablet orally chewed once now
☐ aspirin 325 milligram tablet, delayed release (E,C) orally once a day
☐ Aspirin contraindicated because:
☐ clopidgrel 300 (4x75) milligram tablet orally once 4 tablets
☐ clopidgrel 75 milligram tablet orally daily
☐ Morphine 0.5mg IV Push every 2 hours as needed for pain scale
☐ Consider for non-PCI candidate patients (see evidence):
☐ Integration 180 UG/kg bolus intravenously now
☐ Integration 2 ug/kg/min intravenously for 72 hours

*FIG. 3F*

Stone
Stepping Checkout system  ⌂home 🔒sign off ? guide
QUICKORDERS
Patient ⟩ Problems ⟩ Orders ⟩ Review   The Problem-Based Order Writing System Test Patient / MR=5315315

Step 4: Review

No "Code" orders have been written
No allergy information documented

Orders

Admit
- Admit to Inpatient (Acute), Medical/Surgical  [MdSrg]
- Admit ting service / admitting MD / *:  [MdSrg]

Diagnosis
- Diagnosis: Unstable Angina/NSTEMI  [UAng]
- Diagnosis: Diabetes Mellitus  [DM]
- Diagnosis: Chronic Kidney Disease / Chronic Renal Insufficiency  [CKD]

Vitals
- Vital Sign per protocol  [UAng]

Nursing
- Smoking Cessation Education Screen for smoking with cessation therapy if indicated  [UAng]
- If blood glucose greater than 150 mg/dL, initiate sliding scale insulin per physician order  [DM]
- Notify MD if blood glucose less then 60 mg/dL  [DM]
- Finger stick glucose (qAC and qHS)  [DM]
- Obtain intern health care proxy  [MdSrg]

Diet

ORDER SETS HAVING DIFFERENT VIEWS FOR CPOE SYSTEMS

CROSS-REFERENCE TO RELATED APPLICATIONS

This application claims the benefit under 35 U.S.C. §119 of Provisional Patent Application No. 60/878,379, entitled "QUICK ORDERS SYSTEM FOR FACILITATING TREATMENT PLAN CREATION BY DOCTORS", filed Jan. 3, 2007, incorporated by reference herein in it entirety.

BACKGROUND OF THE INVENTION

1. Field of the Invention

The present invention generally relates to medical and hospital information systems. More specifically, it relates to computer systems and methods for use by doctors in treating patients.

2. Description of the Related Art

There has been an increasing need to reduce medical errors in hospitals and clinics. Responding to public concern over such errors, and seeking to standardize care around best practices to control quality and cost, American hospitals are purchasing costly clinical information systems installed with a technology known as Computerized Physician Order Entry (CPOE). Current estimates are that 10% of US hospitals have CPOE systems and the number is expected to grow to 20-30% in the next few years.

However, CPOE systems require a certain type of structured data to operate successfully. Manual entry of this data in the required format has proven very impracticable for busy healthcare professionals (hereinafter "physicians") in the front-lines. Thus, the success of these systems has relied heavily upon pre-built templates referred to as order sets, a term known in the field of medical/hospital software development. Order sets, described in greater detail below, essentially offer templates of care for the most common diagnoses and procedures. Utilizing a checklist approach, they allow physicians to rapidly select the appropriate options for care in a structured data format. Order sets are critical to successful implementation of CPOE systems, and companies (ZYNX of Santa Monica, Calif., Healthgate of Burlington, Mass.) are in the business of supplying content for CPOE order sets.

Current order sets are generally designed for single diagnoses and organized in a rigid fashion. For example, a hospital may have separate order sets for "Community Acquired Pneumonia Admission", "Appendectomy Postop" and "Congestive Heart Failure Admission". However, an aging population and increasing success in managing chronic conditions over the long-term is resulting in a patient population that presents to hospitals with multiple comorbidities. For example, a patient may present with an acute pneumonia, but that pneumonia is superimposed upon chronic diabetes, peripheral vascular disease and emphysema. Furthermore, critically ill patients often require physicians to design a treatment plan by physiological system (cardiovascular, neurological) rather than by diagnosis to ensure that critical interrelationships aren't missed. For these complex patients, physicians often plan diagnosis and treatment using an internal mental model based around solving for multiple medical problems/conditions or around physiological systems, thereby creating a serious mismatch with conventional order sets which are designed for a single diagnosis in a traditional functional framework. Thus, the current state of the art forces physicians to develop treatment plans using a checklist around a single diagnosis. In contrast, there is a strong need by physicians for systems (CPOEs, order sets, etc.) that are better able to map to these different internal mental models for managing complex patients.

SUMMARY OF THE INVENTION

In one embodiment, a method of creating order set content so that order sets can be viewed from varying perspectives is described. An order set library is modified such that each order statement or orderable is tagged with metadata. In the described embodiment, each orderable is tagged with an Intervention tag, a Problem tag, and a System tag. An application may then take the modified order sets and present them to doctors based on an Intervention view, a Problem view, or a System view. These views give the doctor the option of switching between views depending on the severity of a patient's medical condition and allows the doctor to follow a more intuitive and internal mental process when treating a patient. The doctor does not have to translate between different perspectives of the order sets mentally, thereby greatly reducing the doctor's cognitive load.

Other embodiments of the invention pertain to computer program products, including tangible, machine-readable medium, including various forms and implementations of volatile and non-volatile memory, on which are stored program instructions for implementing any of the methods described herein. Any of the methods, processes, sub-processes, threads, formulas, calculations, and the like of this invention may be represented as program instructions and/or databases, data structures, data tables, and so on that can be provided on such computer readable media.

These and other features and advantages of the present invention are described below with reference to the drawings.

BRIEF DESCRIPTION OF THE DRAWINGS

References are made to the accompanying drawings, which form a part of the description and in which are shown, by way of illustration, particular embodiments:

FIGS. 3A to 3F are screen displays of showing various stages of creating and viewing order sets from three perspectives: Intervention, problem, and System, in accordance with one embodiment of the present invention.

DETAILED DESCRIPTION OF THE INVENTION

Figure 1:
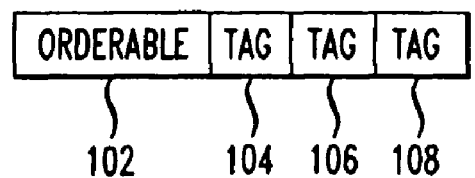
FIG. 1 is a block diagram showing an orderable having a plurality of tags in accordance with one embodiment of the present invention.

Methods and systems for creating and viewing order set content that may be displayed in various views based on a physician's alternative strategies for task accomplishment, mental processes and intuitive cognitive analysis, for example by medical problem or by physiological system are described in the various figures. In one embodiment, conventional order sets are disassembled and re-assembled to reflect different views on the underlying content, views which may reflect medical Interventions, medical Problems (including hospital unit admission), and physiological Systems. In other embodiments, fewer or additional criteria may be used to re-assemble views depending on various factors, such as practice area (e.g., surgery) or setting/unit (e.g., ER).

Before proceeding with various embodiments of the present invention, it is helpful to describe an order set in more detail. An order set is a collection of order statements, instructions and reminders, typically related to a specific hospital unit or medical condition. These statements, instructions and reminders collectively referred to herein as "orderables." Thus, an order set is a group or list of orderables. Typically, medical conditions/problems and hospital admissions have corresponding order sets. For example, an ICU unit may have an ICU Admission order set (an order set for admitting a patient to a specific hospital unit) or Congestive Heart Failure has an order set (order set for a medical condition).

As is known in the art, the number of potential orderables (e.g., notes, reminders, order statements, options, etc.) for a particular condition can total in the dozens or even hundreds in rare cases. Thus to help organize this mass of undifferentiated content, these orderables are traditionally parsed into categories, which may be referred to generally as orderable categories. The traditional orderable categories used in many hospital CPOE Systems include:

Admit
Diagnosis
Condition
Vitals
Allergies
Activities
Nursing
Diet
IV Fluids
Medications
Laboratories
Diagnostics
Consults/Other In other embodiment, there may be fewer or additional orderable categories depending on the CPOE System and hospital needs. The list provided here is illustrative of one example of categories to which orderables may be assigned.

In the art of order set creation and CPOEs, there is no standard name for a group of categories. In one embodiment of the present invention, these orderable categories are referred to as Interventions. Thus, "Admit" is an Intervention, "Nursing" is an Intervention, "Medications" is an Intervention, and so on.

In the described embodiment of the present invention, when a physician begins treatment of a patient, one or more views on the underlying order set content are created. This is particularly beneficial for patients having intermediate to high complexity in their medical problems, where the physician may want to view the underlying order set content from different perspectives. Viewing the order set content using only the traditional intervention-based model is not efficient for the physician. Additional views on the order set are likely to facilitate treatment and diagnosis. These additional views are of the same underlying order set content, that is, each view shows the same orderables organized in a different way. The order set is used as input to a CPOE system at the hospital.

If the patient has a single medical problem, orderables in an order set may be organized and presented to a physician by Intervention:

Intervention A
  Orderable n
  Orderable x
  Orderable h
  Intervention D
  Orderable b
  Orderable u Intervention F
  Orderable k
  Orderable p . . . .

This organizational structure may be sufficient and intuitive for the physician when treating patients having a single medical challenge or problem. However, when organizing an order set for a patient afflicted with multiple, complex medical conditions, structuring the orderables based solely on Intervention is not intuitive to a physician and may be misaligned with how she is normally trained to treat and diagnose these challenging clinical situations.

A physician may approach treatment of a patient based on the severity of the medical challenges facing the patient. For example, for a patient having multiple medical problems, a doctor typically derives a course of action by thinking of each medical problem or challenge separately: What should be done for the patient's pneumonia? What needs to be done in addition for the patient's diabetes? The patient needs to be admitted to the Intensive Care Unit. What needs and issues does that raise? And so on. Here the doctor is sequentially isolating and solving each medical challenge and/or problem and hospital unit admission needs/requirements (collectively referred to as "medical problems"). This strategy of "divide-and-conquer" is a common technique for experts in many fields to deal with complex problems involving multiple variables. Illustrative lists of hospital units and medical problems/challenges are provided below.

In another example, a patient may have multiple medical problems that are more severe or life-threatening. In these serious situations, various medical problems begin to interrelate and impact upon each other, and thus a doctor may approach treatment based on physiological system, the goal being to review the entire organism and prevent any one or more systems from failing. In these more intense and critical scenarios, the doctor's mental processes have transitioned from or surpassed thinking of an order set based on intervention or even by medical problem. Here the doctor's intuition and mental processes may be described as being at a system level and it is most beneficial in these situations if order sets are organized according to these mental processes, rather than processes geared toward interventions and problems. Examples of Systems are:

Cardiac (Cardiovascular)
  Respiratory (Pulmonary)
  Neurologic
  Gastrointestinal
  Endocrine
  Heme/ID (Hematology/Infectious Disease)
  FEN (Fluids, Electrolytes, Nutrition)
  +/−Musculoskeletal
  ICU Care The mental work of translating and mapping an internal model to a different structure in an order entry system is termed cognitive load. Increased cognitive load on physicians contributes to errors in care delivery. In providing alternate views on the underlying order set content that map more closely to the way that physicians intuitively approach clinical situations, the various embodiments of the present invention seek to reduce cognitive load on the physician.

An order set organized based on Intervention may be as follows, using the example of the three orderables provided above ("Start 16 gauge IV now", "CBC test in AM" and "Do not use >2 grams of acetaminophen in patients with liver dysfunction".) The brackets [ ] indicate that the orderable may be selected and the asterisk * indicates that the orderable is a note or reminder and is not selectable.

NURSING
   [ ] Start 16 gauge IV now
MEDICATIONS
   Do not use >2 grams of acetaminophen in patients with liver dysfunction"
LABORATORY
   [ ] CBC test in AM As described above, a medical problem (including admission to a hospital unit) has an order set. Thus, patients having multiple medical problems will have multiple order sets associated with their treatment and to which the physician will be referring to for treatment. An order set view that result from mechanically merging or collating numerous other orders sets result in a single order set presentation or view that is brittle, artificial, and, moreover, misaligned with the mental thought processes of physicians when treating patients with intermediate and severe medical challenges and symptoms. A physician may struggle to transition back-and-forth between her trained, internal thought processes (which may be guided by medical problem and/or System, as described above) and the choices, reminders, notes, etc. presented by an order set organized by Intervention alone that is viewed by the physician on a monitor. These mental transitions detract from the critical decision-making called for by the physician at the time of treatment and may cause confusion for the doctor and result in errors or misdiagnosis.

Being able to view merged order sets based on medical problem or System in complex medical cases (and relatively simple ones) may significantly reduce the cognitive load on the physician and allows the diagnostic and treatment planning process to be more intuitive to the physician.

In one embodiment of the present invention, a service provider obtains order sets for all (or some) of the medical problems defined for a particular hospital. As described above, each medical challenge, problem, condition and hospital unit admission (collectively referred to as "medical problem") may have an associated order set. As a side note, not all hospitals treat the same medical problems or have identical units, thus medical problems—in the CPOE sense—may differ from hospital to hospital.

Below is an example of a physician treating a patient already in the hospital's database system. The physician logs into the database system at the hospital. The database system may be operating in conjunction with the hospital's CPOE system. Once the doctor logs into the system, she selects a patient. After selecting a patient, the doctor selects the appropriate level of care reflecting the level or intensity of care that may be required. For example, should the patient go to the Med Surgical unit for comparatively low intensity care, the Coronary Care Unit (for intermediate care including special cardiac monitoring) or the Intensive Care Unit (for critically ill patients requiring the highest levels of care)? The types of units and their names may vary in different hospitals, but the general number may be from five to eight units. Examples of hospital units include:
   Med/Surg
   Telemetry (CCU, Coronary Care Unit)
   Intensive Care (ICU, Critical Care)
   PACU (Post-Anesthesia Care Unit)
   NICU (Neonatal Intensive Care Unit)
   PICU (Pediatric Intensive Care Unit)
   OR (Operating Room)
   ER (Emergency Room, ED)
   Others depending on facility After selecting the appropriate unit for care, a typical next step may be to identify the primary medical challenges and symptoms facing the patient, termed a Problem List. The number of problems from which a doctor may select varies depending on how a problem is defined. It is helpful to note that there are roughly 10,000 human diseases. However, the concept of "problem" is not simply a disease. It is any "challenge" that the physician needs to manage for a patient. Thus, problems may also include symptoms that have not been diagnosed yet (chest pain), or monitoring or instituting prophylaxis to prevent later appearance of diseases/complications that appear during hospitalizations such as deep venous thrombosis or urinary tract infections. For example, a patient may not have bedsores on arrival, but if the patient is lying in bed for several weeks, that will become a problem, sometimes referred to as hospital care issues. Some physicians may anticipate these hospital care needs and list them as a problem to be monitored and prevented before it happens.

Often there are several hundred medical challenges from which a doctor may choose. Furthermore, different medical specialties are trained to diagnose and manage their patients in different ways. In one embodiment, there are user interfaces that have specific features that facilitate the creation of Problem Lists for patients based on the specialty of the physician using the system. For example, a hospitalist (trained in Internal Medicine) may assemble a Problem List by thinking about Hospital Unit, Primary Problems and Hospital Care challenges. An Emergency Medicine physician may plan their Problem List around Primary Complaint and ER Care, while a surgeon may assemble their Problem List by Surgical Procedure and Associated Comorbidities. Once diagnosis is complete and a Problem List has been created, a doctor may consider potential issues that may arise in the hospital, often referred to as hospital care problems, after care or treatment has begun for a patient, for example, from transfusions, bed rest, and so on. These hospital care problems may be added to the problem set derived in the previous step.

Issues arise when orderables that are categorized into Interventions are used beyond the "single" medical problem context, for which the Intervention view may be adequate. However, when dealing with multi-problem patients or more complex cases, categorization based on Intervention alone is counterintuitive.

When a patient is critically ill, the doctor may frame her mental process regarding treatment around physiological System to ensure that all Systems are supported properly so that the patient can at least stabilize. As explained above, the doctor may think of what to do to ensure that the patient's Cardiovascular System is supported properly and that his Respiratory System is functioning. There may be an infection as well, in which case the patient's Immunological or Hematological Systems may need attention. In this scenario, the doctor is essentially 'thinking by System' with respect to treating the patient.

In one embodiment of the present invention, metadata is associated with each orderable. An orderable already has one metadata category associated with it, namely, Problem(s). Using an abstract example to illustrate, a medical problem X has orderables a, b, and c in its order set. Each order statement a, b, and c will likely have many medical problems (hundreds or thousands) listed in the metadata category.

| Orderable | Metadata Tags Problems |
|---|---|
| a | X |
| b | X |
| c | X |

In one embodiment, a service provider associates or tags at least two other metadata tags with each orderable, namely, Intervention and System. Thus, each orderable a, b, and c will be tagged with medical problem X and with Intervention Y and System Z.

| Orderable | Metadata Tags | | |
|---|---|---|---|
| | Problems | Interventions | Systems |
| a | X | Y | Z |
| b | X | Y | Z |
| c | X | Y | Z |

By providing these metadata tags for each orderable, the system can take the underlying order set content and reassemble into different views based on these Metadata tags, enabling the doctor to view order sets based not only on intervention alone, but by interventions within a sequence of medical problems and on physiological system through a user interface, described below. The orderables may be reorganized dynamically by clicking on icons on the interface and are displayed in different views of the order sets. The doctor does not have to perform any internal mental steps to translate or transition among medical problem, intervention, and system, depending on the circumstance.

For example, order sets displayed by PROBLEM may appear as:

[BY PROBLEM]
  PNEUMONIA
    Do not use >2 grams of acetaminophen in patients with liver dysfunction"
    [ ] CBC test in AM
  DIABETES
    (nothing)
    ICU Admission
    [ ] Start 16 gauge IV now Or, an order set based on System may be displayed:

[BY SYSTEM]
  FLUIDS, ELECTROLYTES AND NUTRITION
    [ ] Start 16 gauge IV now
  HEMATOLOGY/INFECTIOUS DISEASE
    [ ] CBC test in AM
  GASTROINTESTINAL
    Do not use >2 grams of acetaminophen in patients with liver dysfunction"

Thus, as described above, the same underlying content from the original order set organized by Interventions is being used, however new order sets based on problem or System may be created on demand by the doctor.

In one embodiment, an order set is presented in a problem view where orderables are presented by problem and within each problem, by a specific order of Interventions. Thus, in this specific embodiment, the Intervention categories are utilized but not in the same manner as they are for presenting Intervention-only based views. In an example where a patient has one medical challenge or problem, a Problem-based view of the order set would have only one problem or challenge listed and within that problem, a list of orderables, in this case two:

[BY PROBLEM]
  PNEUMONIA
    Do not use >2 grams of acetaminophen in patients with liver dysfunction"
    [ ] CBC test in AM In the Problem view, the orderables are listed according to Interventions, but not in the sequence of Interventions as provided for in the Intervention view, which is Admit
Diagnosis
Condition
Vitals
Allergies
Activities
Nursing
Diet
IV Fluids
Medications
Laboratory
Diagnostics
Consults/Other,
but rather in the following sequence:
Medications
Laboratory
Nursing
All Other . . . .

This sequence of Interventions, used in the Problem-based view, is more likely to follow the physician's mental process when examining and treating a patient. Intuitively, a physician is likely to first determine what "meds" are needed, second, whether any lab work or testing needs to be done, and then think about care and nursing needs, followed by other actions/Intervention, the order of which may not be critical or may vary depending on the challenge.

In one embodiment, the Problem view does not insert the Intervention name in the list, as in the example above. In another embodiment, the Intervention name is used to delineate the orderables. For example:

[SINGLE PROBLEM]
  PNEUMONIA
    Medications:
      Do not use >2 grams of acetaminophen in patients with liver dysfunction"
    Laboratory:
      [ ] CBC test in AM For patients with multiple challenges, the problems are listed in an order specified by the physician. The challenges are dealt with sequentially, one after the other. This is how physicians intuitively plan their treatment of patients with multiple problems. For example, for a patient having a heart attack and with diabetes, the physician will address the heart attack first. Using the example from above:

[MULTIPLE PROBLEM]
  PNEUMONIA
    Do not use >2 grams of acetaminophen in patients with liver dysfunction"
    [ ] CBC test in AM
  DIABETES
    (nothing)
    ICU Admission
    [ ] Start 16 gauge IV now With respect to inserting Intervention names within the list of orderables for each challenge, the same two options may apply, namely, insert the name, thereby creating another level of organization, or omit them, as in the example above.

The following examples illustrate one embodiment of the present invention. For a patient having a single medical challenge, such as a Heart Attack, sample orderables are:
EKG
Cardiac monitor
Aspirin 325 mg by mouth daily
In the INTERVENTION VIEW, the order set would appear as follows:
Admit
Diagnosis
Condition
Vitals
    Cardiac monitor
Allergies
Activity
Nursing
Diet
IV Fluids
Medications
    Aspirin 325 mg by mouth daily
Laboratory
    EKG
Consults
In the PROBLEM VIEW:
Medications
    Aspirin 325 mg by mouth daily
Laboratory
    EKG
Nursing
All Other
    Cardiac monitor
In the SYSTEM VIEW:
Cardiac
    Aspirin 325 mg by mouth daily
    EKG
    Cardiac monitor
Respiratory
Gastrointestinal
Neurologic
FEN/Renal
Endocrine
Heme/ID
ICU Care In the examples below, different order set views for a patient having two medical challenges, Heart Attack and Diabetes, are shown. Sample orderables for Acute Myocardial Infarctin (AMI) are EKG, Cardiac monitor, and Aspirin 325 mg by mouth daily. Sample orderables for Diabetes (D) are Finger stick glucose daily, Insulin Sliding Scale, and HbA1c test.
In an INTERVENTION VIEW, the order set would appear as follows:
Admit
Diagnosis
Condition
Vitals
    Cardiac monitor (AMI)
Allergies
Activity
Nursing
    Finger stick glucose daily (D)
Diet
IV Fluids
Medications
    Aspirin 325 mg by mouth daily (AMI)
    Insulin Sliding Scale (D)
Laboratory
    EKG (AMI)
    HbA1c test (D)
Consults
In the PROBLEM VIEW:
HEART ATTACK
Medications
    Aspirin 325 mg by mouth daily
Laboratory
    EKG
Nursing
All Other
    Cardiac monitor
DIABETES
Medications
    Insulin Sliding Scale
Laboratory
    HbA1c test
Nursing
    Finger stick glucose daily
All Other
In the SYSTEM VIEW:
Cardiac
    Aspirin 325 mg by mouth daily (AMI)
    EKG (AMI)
    Cardiac monitor (AMI)
Respiratory
Gastrointestinal
Neurologic
FEN/Renal
Endocrine
    Finger stick glucose daily (D)
    Insulin Sliding Scale (D)
    HbA1c test (D)
Heme/ID
ICU Care FIG. 1 is a block diagram showing an orderable 102 having a plurality of tags, 104, 106, and 108 in accordance with one embodiment of the present invention. As described above, these tags may represent a Problem, an Intervention, and a System. In other embodiments, other criteria may be used for tags, also referred to as metadata tags. These tags are used to efficiently create different views of an order set as desired by the physician. The software executing on a hospital computer system may use these tags to facilitate creation of various views as shown in greater detail in FIGS. 3A to 3F below. In one embodiment, the orderables and their metadata tags are stored in a relational database system in the hospital computer system. They may also be stored in a flat file, a VSAM file, in a hierarchical database, or any other suitable database or file structure depending on the computer system. Example computer systems and storage media are described in FIGS. 4A and 4B.

Figure 2:
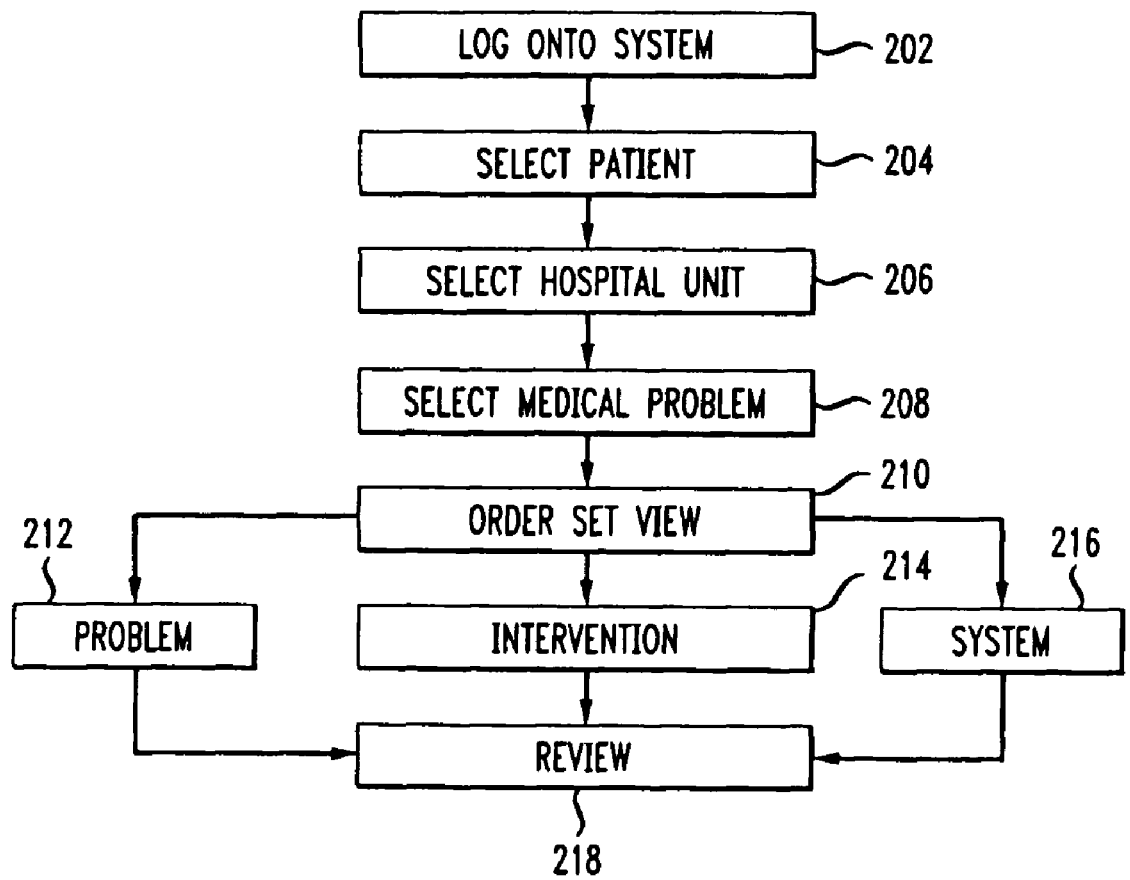
FIG. 2 is a flow diagram of a process taken by a physician or user in creating and viewing order sets in accordance with one embodiment of the present invention.

FIG. 2 is a flow diagram of a process taken by a physician or user in creating and viewing order sets in accordance with one embodiment of the present invention. A user interface for implementing these steps are described in the screen shots described in FIGS. 3A to 3F. At step 202 a physician logs onto the hospital computer system and, specifically, the order set viewing software of the present invention. At step 204 the doctor selects a particular patient (presumably, identification information for a new patient has already been entered for new patients). At step 206 a physician may begin by selecting which hospital unit the patient should be admitted to. As described above, a hospital unit selection is part of the process of creating a Problem List. Once the hospital unit has been selected, the doctor may select specific medical challenges or problems at step 208. Thus, at the end of step 208, a medical Problem List has been created. At step 210 the physician may select a particular view of the resulting order sets. In the described embodiment, there are three views: Problem (212), Intervention (214), and System (216). The physician may view the order sets in any one of these views and switch among them using the user interface described below. Once the physician has created an order set and viewed it in one or more views, at step 218 the order set is reviewed and printed or saved as needed.

Figure 3D:
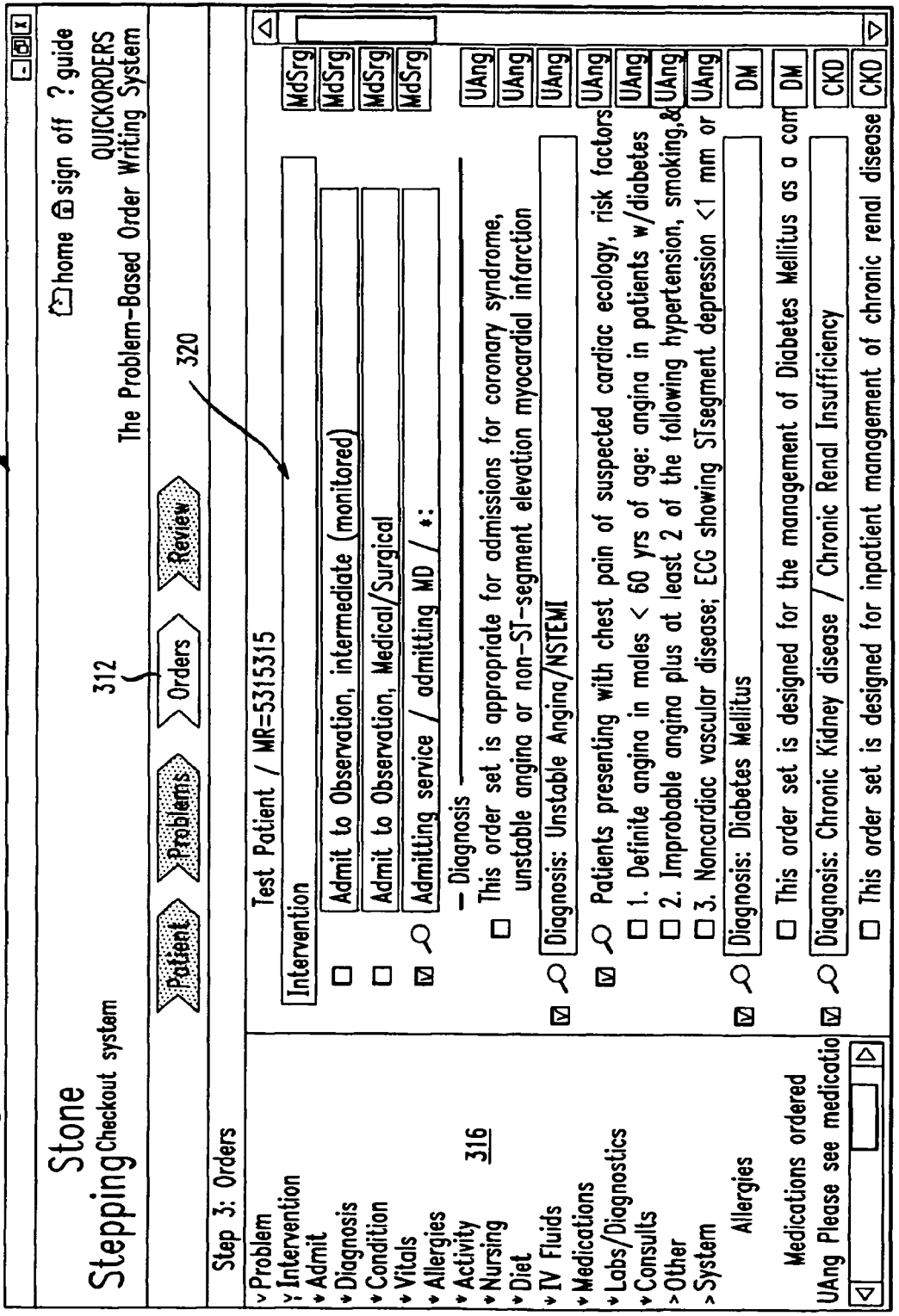

FIGS. 3A to 3F are screen displays of showing various stages of creating and viewing order sets from three perspectives: Intervention, problem, and System, in accordance with one embodiment of the present invention. After a physician logs into the system and selects a patient, the process of creating order sets for the patient begins. FIG. 3A shows a screen 300 for selecting problems as shown by stage icon 302 ("Problems") that allows a physician to select a hospital unit to which the patient will be admitted in area 304 ("Admit to") and to identify which problems have been diagnosed in area 306 ("Primary problems"). In "Admit to" area 304, hospital units and brief descriptions are provided and a check box allowing the user to add any selected unit's order set to the orders. In "Primary problems" area 306 the physician can select a medical problem/condition from the list, each problem selection having "Specialty", "Phase of care", "Times used", "Favorite" and an icon for getting further details. In other embodiments more or fewer details may be provided, screen 300 being merely one example of a user interface for implementing the present invention.

FIG. 3B is a screen shot 308 after a physician has selected a unit (e.g., Med/Surg) for admission in area 304 and certain medical problems, such as Diabetes Mellitus (DM), Unstable Angina/NSTEMI, and Chronic Kidney Disease (CKD) (CRI), and possibly others in area 306, highlighted after being selected.

FIG. 3C is a screen shot 310 of the "Orders" stage of the process, as shown by stage icon 312 in accordance with one embodiment of the present invention. A "Problem" display area 314 shows a Problem view of an order set. Under "Problem" in area 314 the medical problem "Unstable Angina/NSTEMI" is listed. The orderables are listed according to a specific sequence of Interventions as described above (Meds, Labs, Diagnosis, Care, etc.). The first category of orderables is provided under "Medications." On the left side of screen 310 is a summary listing of the medical challenges under "Problems" indicating that the user is seeing a Problem view of the order set. The other order set views, Intervention and System, are listed below Problems.

FIG. 3D is a screen shot 318 also showing an "Orders" stage of the process (as indicated by stage icon 312) having an "Intervention" display area 320. The sequence of Interventions is as described above and as shown in area 316 which shows a listing of Interventions in their conventional sequence. In display area 320, the Admit, Diagnosis, and the beginning of the Condition Intervention orderables are shown.

Figure 3E:
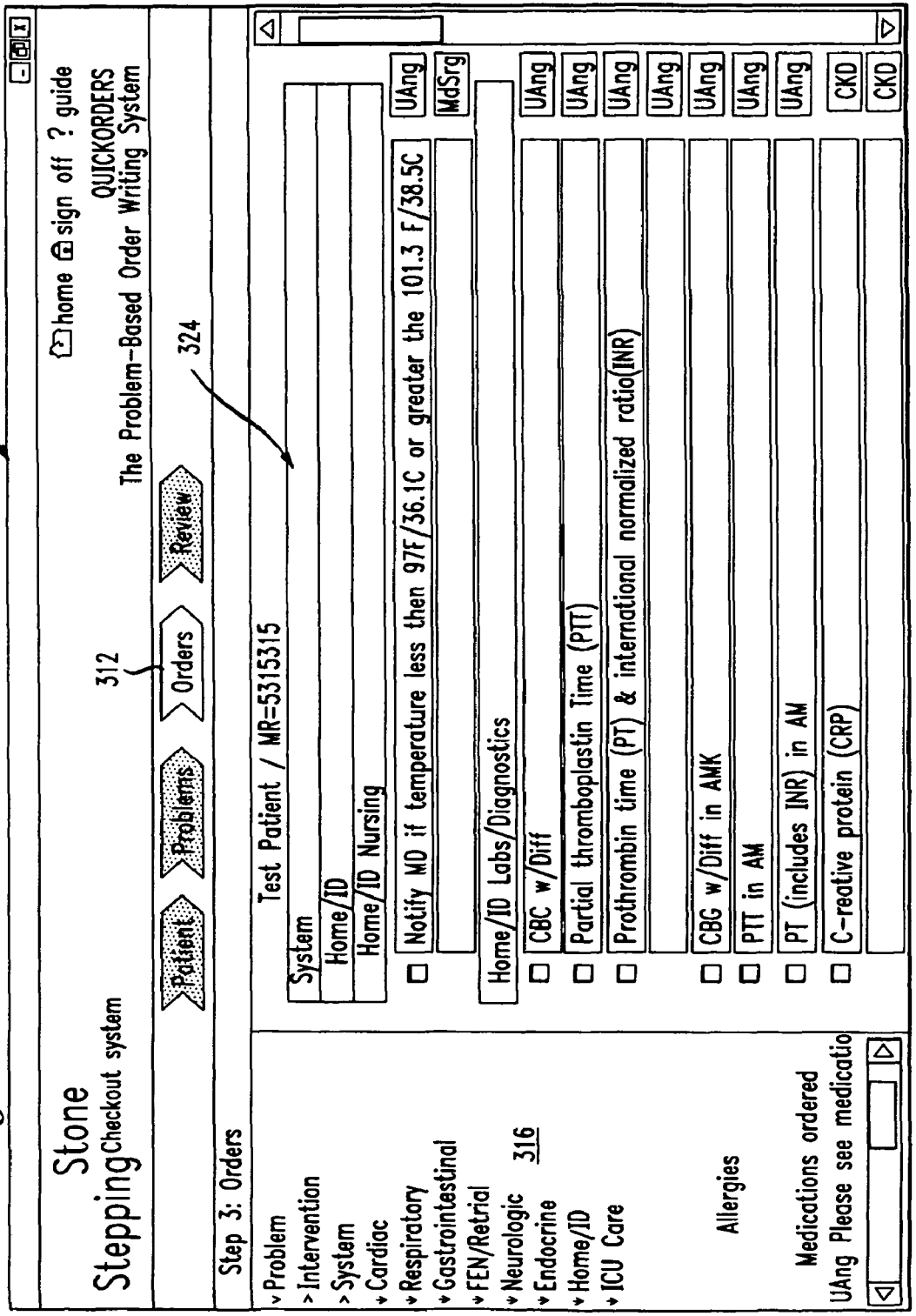

FIG. 3E is a screen shot 322 also showing an "Orders" stage of the process having a "System" display area 324. The first System shown in this example is "Heme/ID" (Hematology/Infectious Disease) and under it, orderables for "Nursing" and "Labs/Diagnostics" that may be selected by the physician. In area 316, as with Problems and Intervention views, a detailed listing of the various physiological Systems under the System view is shown.

It is important to note at this stage that the physician can switch among the views by simply clicking on the name of the view in area 316 in each of the screen shots. By clicking on the view name, a detailed listing of the view appears in area 316 and the order set view appears in the larger display areas to the right. Thus, the physician can easily view order sets according to his or her medical judgment and as internal mental processes change during treatment or diagnosis of a patient. Of course, in other embodiments, the configuration of the display areas and overall presentation of the user interface may vary widely without altering the concept of facilitating the creation of order set views and switching among them as needed.

FIG. 3F is a screen shot 326 of a "Review" stage of the process as indicated by stage icon 328. Screen shot 326 has an area 330 labeled "Step 4: Review" that displays some general information about the order set followed by a display area 332 under "Orders" which show orderables under Interventions (Admit, Diagnosis, Vitals, Nursing, and so on). At the bottom of screen shot 326 is an area of Additional Hospital Forms. After the Review stage, the physician may print or save the order set.

Figure 4A:
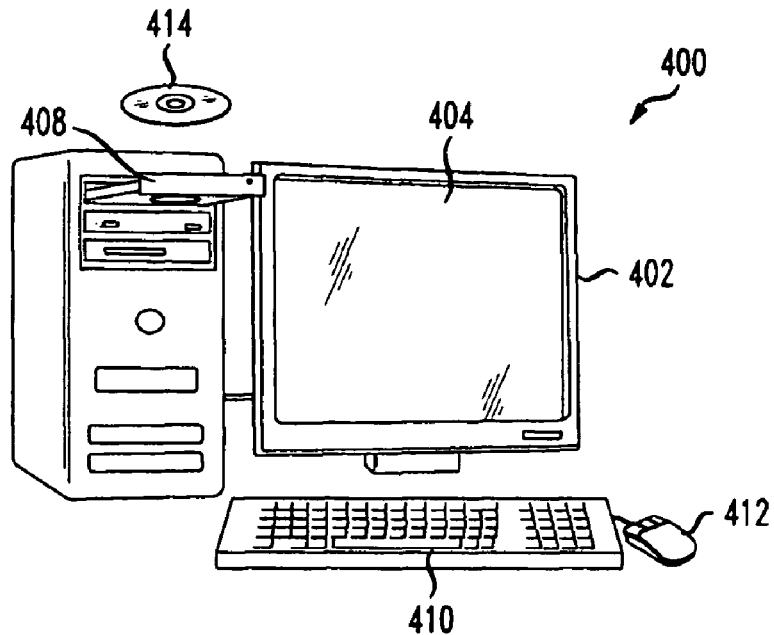
FIGS. 4A and 4B illustrate a computer system suitable for implementing embodiments of the present invention.
Figure 4B:
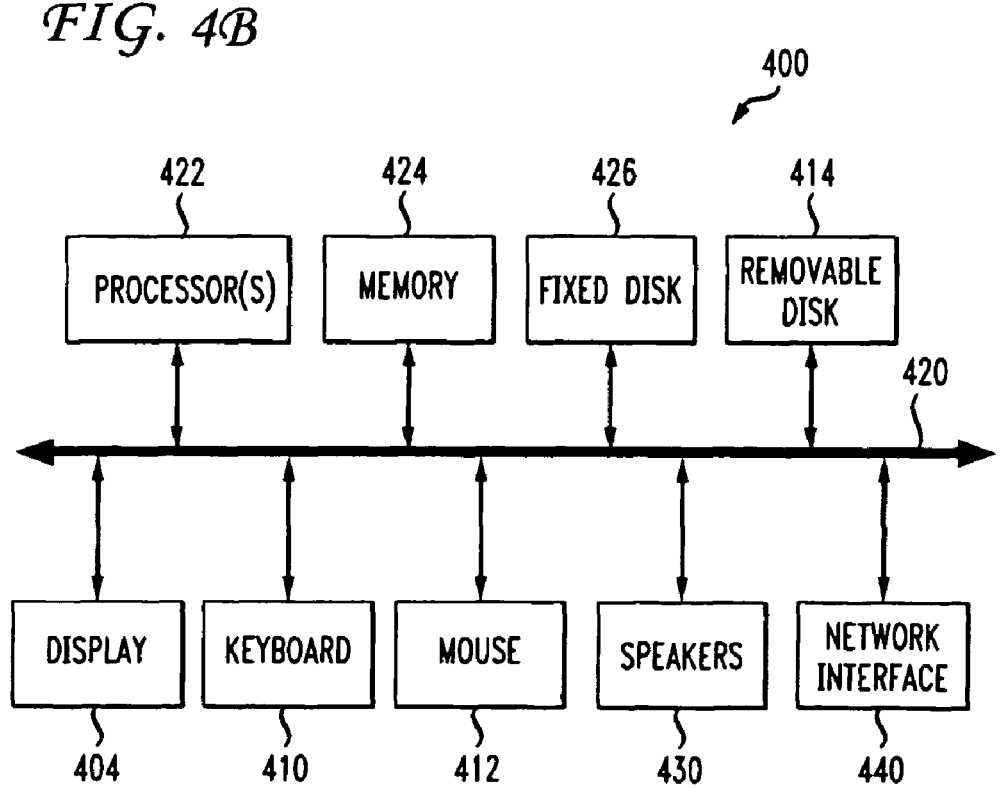

A sample listing of approximately 30 of the most common medical problems/challenges encountered with inpatient care is provided below:

Acute Myocardial Infarction (heart attack)
Congestive Heart Failure
Atrial Fibrillation
Community-Acquired Pneumonia
Nosocomial Pneumonia
Asthma Exacerbation
Chronic Obstructive Pulmonary Disease (COPD) Exacerbation
Stroke—Ischemic
Stroke—Hemorrhagic
Subdural Hemorrhage
Transient Ischemic Attack
Acute Pancreatitis
Lower Gastrointestinal Bleed
Upper Gastrointestinal Bleed
Acute Renal Failure
Chronic Kidney Disease
Pyelonephritis
Urinary Tract Infection
Deep Venous Thrombosis (DVT) Prophylaxis
Health Care Maintenance (including giving immunizations while hospitalized)
Cellulitis
Diabetes Mellitus
Diabetic Ketoacidosis/Hyperosmolar Hyperglycemic
Alcohol Withdrawal
Acetaminophen Overdose
Abdominal Pain
Chest Pain (rule-out AMI)
Dizziness/Weakness
Vaginal Bleeding
Seizure/Altered Level of Consciousness FIGS. 4A and 4B illustrate a computer system 400 suitable for implementing embodiments of the present invention. FIG. 4A shows one possible physical form of the computer system. Of course, the computer system may have many physical forms including an integrated circuit, a printed circuit board, a small handheld device (such as a mobile telephone or PDA), a personal computer or a super computer. Computer system 400 includes a monitor 402, a display 404, a housing 406, a disk drive 408, a keyboard 410 and a mouse 412. Disk 414 is a computer-readable medium used to transfer data to and from computer system 400.

FIG. 4B is an example of a block diagram for computer system 400. Attached to system bus 420 is a wide variety of subsystems. Processor(s) 422 (also referred to as central processing units, or CPUs) are coupled to storage devices including memory 424. Memory 424 may include random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 426 is also coupled bi-directionally to CPU 422; it provides additional data storage capacity and may also include any of the computer-readable media described below. Fixed disk 426 may be used to store programs, data and the like and is typically a secondary storage medium (such as a hard disk) that is slower than primary storage. It will be appreciated that the information retained within fixed disk 426, may, in appropriate cases, be incorporated in standard fashion as virtual memory in memory 424. Removable disk 414 may take the form of any of the computer-readable media described below.

CPU 422 is also coupled to a variety of input/output devices such as display 404, keyboard 410, mouse 412 and speakers 430. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 422 optionally may be coupled to another computer or telecommunications network using network interface 440. With such a network interface, it is contemplated that the CPU might receive information from the network, or might output information to the network in the course of performing the above-described method steps. Furthermore, method embodiments of the present invention may execute solely upon CPU 422 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher-level code that are executed by a computer using an interpreter.

Although illustrative embodiments and applications of this invention are shown and described herein, many variations and modifications are possible which remain within the concept, scope, and spirit of the invention, and these variations would become clear to those of ordinary skill in the art after perusal of this application. For example, although order set views have been described in terms of Problem, Intervention, and System, other criteria or categories may be used to view order sets and may depend on the setting, facility, specialty, or environment in which the software is being used. In another example, the user interface for creating an order set and displaying the views may vary widely and the screen shots described herein are merely one illustration of a user interface suitable for implementing the concepts of the present invention. Accordingly, the embodiments described are to be considered as illustrative and not restrictive, and the invention is not to be limited to the details given herein, but may be modified within the scope and equivalents of the appended claims.

We claim:

1. A method of dynamically re-organizing orderables on a computing device, the method comprising:
receiving patient data stored in a computer memory;
receiving hospital unit data identifying a hospital unit where the patient is being treated, said hospital unit data stored in the computer memory;
receiving patient problem data indicating one or more problems to be managed stored in the computer memory;
creating a re-organized order set using the hospital unit data, the patient problem data, and the patient data, said order set being created by a processor executing in said computing device, said order set including multiple orderables, each orderable having at least two tags, said two tags including two of an intervention frame tag, a problem frame tag, and a system frame tag and a tag purposefully chosen to represent mental processes that a physician uses to treat patients and is used to dynamically re-organize and combine said order set to correspond to information received from an order set library and re-organized such that a specific need of a physician at a specific time is addressed, a tag corresponding to one of the intervention frame tag, the system frame tag, or the problem frame tag that a physician uses to treat the patient, said at least two tags used to re-organize said order set to map to a physician thought process when examining and treating the patient.

2. A method as recited in claim 1 further comprising:
re-organizing the order set into one of a plurality of views.

3. A method as recited in claim 1 wherein a tag corresponds to a thought process for the physician when treating a patient, said tags used to assemble multiple views on a set of orderables.

4. A method as recited in claim 1 wherein the system frame tag is for organizing content by physiological systems, the problem frame tag is for organizing content by specific problem, and the intervention frame tag for organizing content by type of orderable.

* * * * *